United States Patent [19]
Clark

[11] Patent Number: 5,219,528
[45] Date of Patent: Jun. 15, 1993

[54] APPARATUS FOR RAPID IMMUNOASSAYS

[75] Inventor: Carl R. Clark, Rockford, Ill.

[73] Assignee: Pierce Chemical Company, Rockford, Ill.

[21] Appl. No.: 740,936

[22] Filed: Aug. 6, 1991

Related U.S. Application Data

[63] Continuation of Ser. No. 386,226, Jul. 28, 1989, abandoned.

[51] Int. Cl.$^5$ .............................................. B01L 11/00
[52] U.S. Cl. ...................................... 422/101; 422/58; 436/177; 436/809; 435/287
[58] Field of Search ................ 435/39, 293, 292, 311, 435/809, 287; 436/177, 809; 422/58, 68, 101

[56] References Cited

U.S. PATENT DOCUMENTS

| | | | |
|---|---|---|---|
| 4,031,197 | 6/1977 | Marinkovich | 436/513 |
| 4,427,415 | 1/1984 | Cleveland | 436/57 |
| 4,493,896 | 1/1985 | LaMotte, III et al. | 435/287 |
| 4,496,657 | 1/1985 | Coppersmith | 435/287 |
| 4,599,315 | 7/1986 | Terasaki et al. | 435/301 |
| 4,626,509 | 12/1986 | Lyman | 435/287 |
| 4,699,884 | 10/1987 | Noss et al. | 435/287 |
| 4,761,378 | 8/1988 | Godsey | 435/293 |
| 4,834,947 | 5/1989 | Levin | 422/101 |
| 4,895,706 | 1/1990 | Root et al. | 422/102 |
| 4,948,564 | 8/1990 | Root et al. | 422/101 |

FOREIGN PATENT DOCUMENTS

| | | |
|---|---|---|
| 0197729 | 10/1986 | European Pat. Off. . |
| 0233385 | 8/1987 | European Pat. Off. . |
| 8503886 | 9/1985 | World Int. Prop. O. . |

OTHER PUBLICATIONS

Iisselmuiden, et al., Journal of Immunological Method, 119 (1989) pp. 35–43.
Iisselmuiden et al., European Journal of Clinical Microbiology, vol. 6, No. 3 (1987) pp. 281–285.

*Primary Examiner*—James C. Housel
*Assistant Examiner*—Lien Tran

[57] ABSTRACT

An apparatus for use in a ligand-receptor assay procedure for the quantitative determination of the concentration of a target ligand in a liquid sample. The apparatus contains top and middle plates having holes therethrough. The holes in the two plates are in axial alignment and the holes in the middle plate have sidewalls that extend below the bottom surface of the middle plate. The apparatus contains a bottom chamber having an opening on the upper side thereof facing the bottom surface of said middle plate. The chamber contains at least one port extending through a surface thereof to permit a vacuum to be created within said chamber and means for accepting a microtiter plate containing a plurality of wells. When the microtiter plate is positioned within the chamber, the ends of the holes extending beneath the bottom surface of the middle plate are located within the wells. The three members of the apparatus can be secured together in vacuum tight relationship such that when a liquid permeable membrane is placed between the top and middle plates, liquid is placed in the holes in the top plate and vacuum is created in the chamber, the liquid is drawn at a controlled rate directly through the membrane without lateral dispersion, through the holes in the middle plate and, in turn, into the chamber.

7 Claims, 4 Drawing Sheets

APPARATUS FOR RAPID IMMUNOASSAYS

This is a continuation of application Ser. No. 07/386,226, now abandoned, filed Jul. 28, 1989.

FIELD OF INVENTION

The present invention relates to immunoassay procedures and, in particular, to quantitative immunoassay procedures which can be rapidly accomplished in substantially less time than heretofore obtainable.

BACKGROUND

Immunoassay procedures have for many years provided sensitive diagnostic tools for the detection of a variety of substances, generally referred to as ligands. Such procedures are described in a number of articles and texts, an example of which is *Reviews on Immunoassay Technology*, Ed. S.B. Pal, Pub. Chapman & Hall, 1988.

One type of immunoassay procedure, commonly referred to as ELISA, utilizes a solid support such as the well in a plastic plate in accomplishing the assay. A receptor for a target ligand is bound to the solid support. A liquid sample containing the ligand, having specificity for the bound receptor, is then applied to the plate. Following washing and incubation procedures, an enzyme conjugate having binding specificity for the ligand is added to the well. After further rinsing, a substrate is added which develops color on contact with the bound enzyme, the amount of color developed being dependent upon the amount of bound conjugate present which, in turn, is indicative of the amount of target ligand bound to the support. Thus, by measuring the amount of color development and correlating such against known standards, the concentration of ligand in the sample can be determined. In general, conventional ELISA procedures take on the order of five hours or more.

Recently, it has been suggested that the ELISA procedure can be accelerated by utilizing immunofiltration (Ijsselmuiden et al., *Journal of Immunological Method*, 119 (1989) 35–43 and *Eur. J. Microbiol.* 6, (1987) 281). In the disclosed procedure, a nitrocellulose filter is precoated with an antigen. Thereafter, a solution containing the target ligand, in this case an antibody, is drawn through the filter followed by rinsing solutions. Finally, either an enzyme-labeled antibody (Ijsselmuiden (1987)) or $^{125}$I-labeled protein A (Ijsselmuiden (1989), both of which have binding specificity for the target ligand, is applied and drawn through the filter to detect the target antibody bound to the antigen on the nitrocellulose filter.

The device used to accomplish the above described assay is illustrated in the 1989 Ijsselmuiden article. It consists of three blocks of perspex which are clamped together during the assay. The bottom section has an external outlet and a valve, and constitutes a reservoir attached to the upper sections. The middle and top sections, designed to accommodate the nitrocellulose filter between them, contain 32 corresponding holes with a diameter of 5 mm and neoprene "O" rings facing the nitrocellulose sheet to prevent lateral flow.

While Ijsselmuiden appears to describe an immunoassay procedure which has the advantage of rapidity over prior procedures, only the procedure utilizing $^{125}$I detection is quantitative. The enzyme-labeled antibody system (Ijsselmuiden (1987)) yields only a qualitative determination of target ligand. A quantitative procedure having the advantages of rapidity and not necessitating the use of radioactively labeled detection reagents such as $^{125}$I would be desirable. In addition, a procedure having the foregoing attributes which also can utilize commercially available microtiter plates and associated readers for determination of color development would be advantageous.

SUMMARY OF THE PRESENT INVENTION

In accordance with the present invention, there is provided a procedure and related apparatus for rapidly and quantitatively accomplishing immunoassays without the necessity for using a radioactive detection system. Further, in accordance with this invention, standard microtiter plates and associated readers can be used to quantitate the results of the assay.

The present invention embodies the features of filtration, such as illustrated by Ijsselmuiden. But, in addition thereto, it provides means for collecting the colored reaction product of enzyme and substrate in a fashion that permits quantitative measurement of color development in a microtiter plate system to achieve quantitation of target ligand.

Accordingly, the present invention provides an apparatus which can be used for colorimetric ligand-receptor assay procedures to the quantitatively determine the concentration of a target ligand in a liquid sample. Briefly described, the apparatus contains a top member, a middle member and a bottom member in a sandwiched relationship. The top and middle members are plates having holes therethrough and between which a membrane can be placed. When the plates are placed one on top of another the holes are in axial alignment and the cross-sectional area of the holes at the bottom surface of the top plate is greater than the cross-sectional area of the holes at the top surface of the middle plate. Furthermore, the sidewalls of the holes in the middle plate extend below the surface of the plate. As described later, the holes in the middle plate are preferably contained within tubes, herein termed cannulas, which are inserted through openings initially formed in the middle plate.

The bottom member of the apparatus is a collection chamber which has an opening on the upper side which faces the bottom surface of the middle plate. The chamber contains a port through one of its surfaces so that a vacuum can be created within the chamber. The chamber contains means for accepting a microtiter plate containing a plurality of wells. In the assembled apparatus, the ends of the sidewalls of the holes which extend beneath the bottom surface of the middle plate are located within the wells of the microtiter plate. The apparatus contains means for securing the three members together in a vacuum type relationship when a membrane is positioned between the top and middle plates.

In use, the apparatus described above is first assembled with a liquid permeable membrane, to which a receptor can be bound, placed between the top and middle plates, and without the plate containing the wells being positioned in the bottom chamber. The membrane can either have the receptor already bound thereto or a solution containing the receptor can be added to the holes in the top plate. In the later instance, vacuum is then created in the chamber with, for example, a peristaltic pump, so that the solution can be pulled past the membrane at a highly controlled consistent rate.

Having the receptor now bound to the membrane, the liquid sample containing the target ligand is added to the holes in the top plate. As above described, vacuum is applied and the liquid is drawn directly through the membrane, through the holes in the middle plate, and then discharged into the collection chamber. As the liquid sample passes through the membrane, the ligand is bound to the receptor on the membrane. Thereafter, a solution containing an enzyme conjugate which has binding specificity for the target ligand is drawn through the membrane and is, in turn, bound to the target ligand. This step is then followed by a washing step to remove enzyme conjugate which did not bind to the ligand.

After the above described steps, the bottom chamber is separated from the top and middle plates, which remain secured together, and is emptied of any liquid which may be present from previous steps. Then, the microtiter plate is positioned in the bottom chamber and the apparatus is reassembled with the sidewall extensions of the middle plate now extending into the wells of the microtiter plate.

A solution containing a substrate for the bound enzyme, which on reaction therewith gives a colored product, is then added to the holes in the top plate and drawn through the membrane, through the holes in the middle plate and, in turn, is deposited into the wells of the microtiter plate. Sufficient substrate solution is utilized so that on collection in the wells the solution extends above the bottom ends of the sidewall extensions. This feature is important in order to insure that the volume of solution transferred from the holes in the upper plate to the wells in the microtiter plate is the same for each set of holes and wells in the apparatus. In turn, this permits measurement of well to well differences in color intensity which correlate to differences in bound ligand. After collection is complete, the bottom chamber is again separated from the remaining structure, the microtiter plate removed from the chamber and the development of color of the solution in the wells determined.

DESCRIPTION OF PREFERRED EMBODIMENTS

Figure 1:
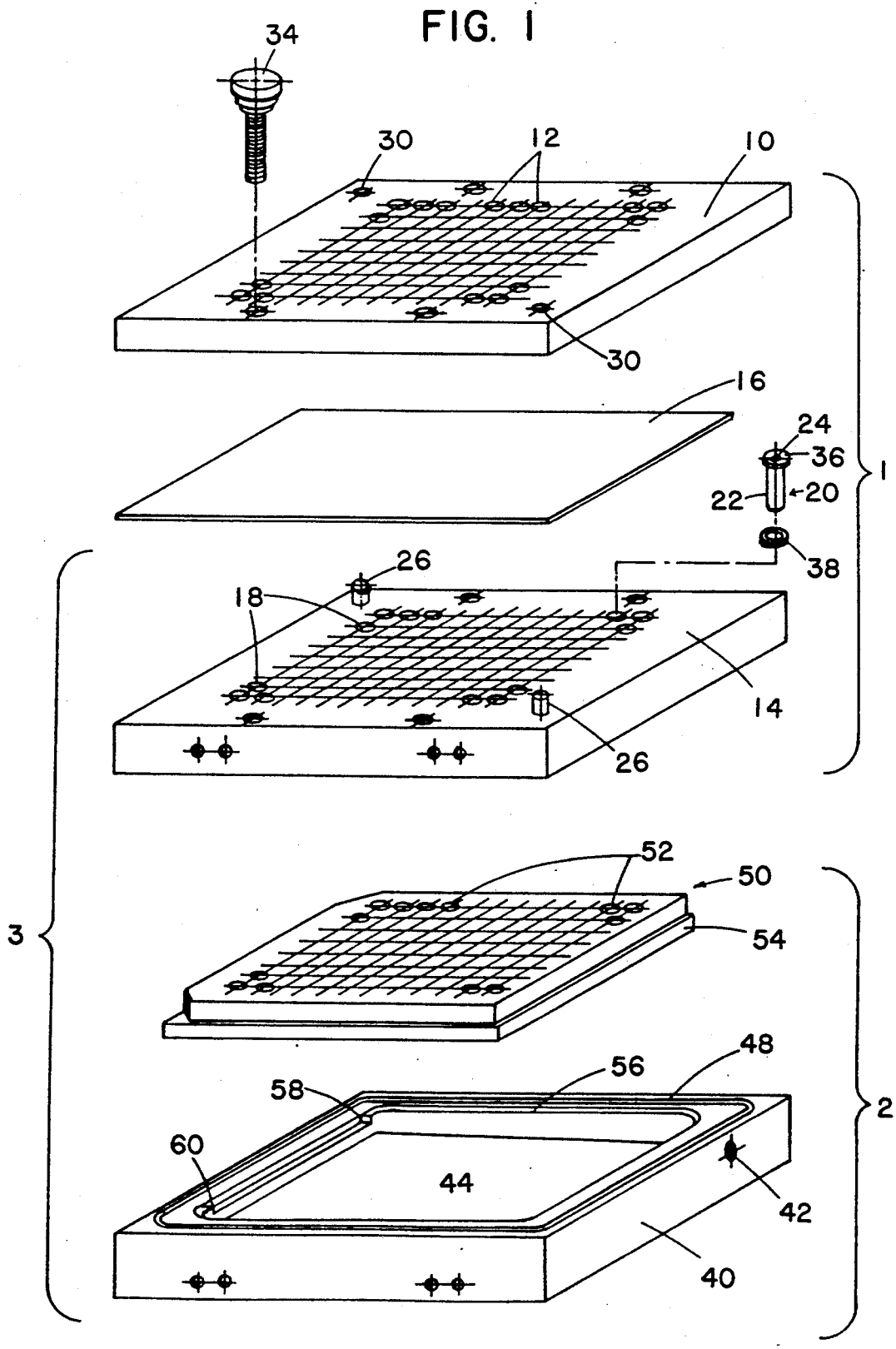
FIG. 1 is an exploded perspective view showing the apparatus of the present invention with certain parts omitted and with a membrane included.

The apparatus illustrated in the drawings is shown to comprise as a top member a sample application plate 10 having a plurality of holes 12 extending therethrough into which a liquid sample can be placed. The middle member is a membrane support plate 14 positioned beneath the plate 10 with the liquid permeable membrane 16, when present, being placed between the two plates. The membrane support plate 14 has openings 18 into which the cannulas 20 are inserted. As shown, each cannula has a sidewall portion 22 with a hole 24 extending through the cannula. As assembled, the holes 12 in the application plate 10 are in axial alignment with the holes 24 in the cannulas 20 located in the support plate 14. In order to attain registry of the two plates 10 and 14 to achieve the aforementioned alignment, the support plate contains studs 26 which are adapted to fit into the holes 30 of the application plate. Four thumb screws 34 serve to secure the application plate 10 and membrane support plate 14 together.

Figure 3:
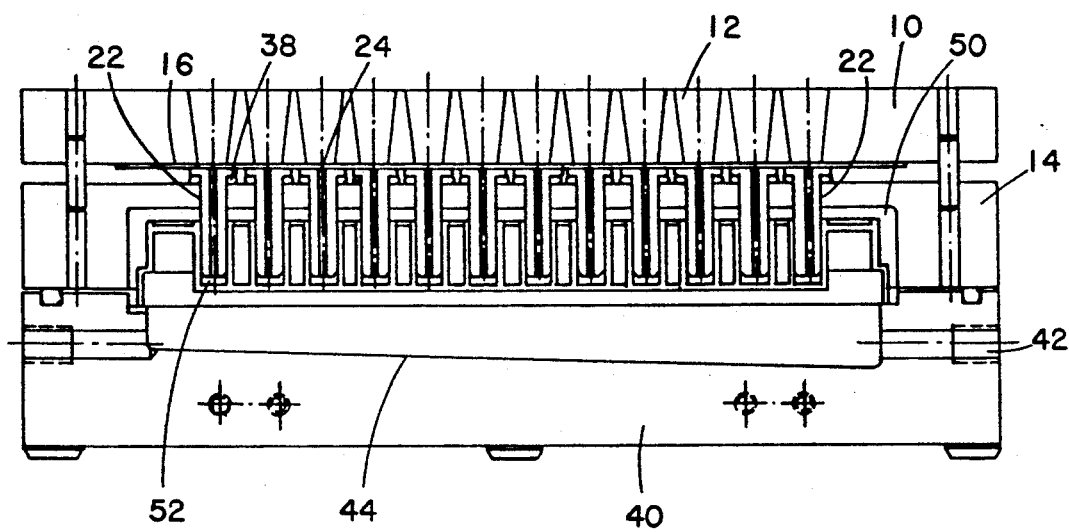
FIG. 3 is cross-section taken vertically through the apparatus.

Turning to the cannulas 20, as mentioned, they contain a sidewall portion 22 and a hole 24. As shown in FIG. 3, the sidewalls 22 of the cannulas extend beneath the bottom surface of the support plate 14. In addition, as illustrated, the sidewalls of the cannulas extend above the top surface of the middle plate, the top end of the cannulas containing a flanged portion 36 which abuts against the membrane 16.

To permit easy application of liquid to the holes 12 in the application plate, the holes are conically shaped and, as illustrated, the cross-sectional area of the holes 12 at the bottom surface of the plate 10 is greater than the cross-sectional area of the holes 24 at the top surface of the cannulas 20. The cross-sectional area of the flanged portion 36 of the cannulas 20 is greater than the cross-sectional area of the holes 12 at the bottom surface of the application plate. These features, in combination, assure that liquid applied in the holes 12 will be drawn through the membrane 16 and, in turn, through the holes 24 in the cannulas 20.

In order to assure that liquid, when being drawn through the membrane 16, does not disperse laterally and cause cross-contamination between samples, flexible "O" rings 38 are placed below the flanged portion 36 of the cannulas between the flanged portions and the membrane support plate 14. Alternatively, instead of the illustrated individual "O" rings, other gasketing means can be used to prevent lateral dispersion of liquid through the membrane. Another example is a flexible perforated diaphragm, having dimensions co-extensive with the array of holes in the top plate, which can be disposed on either or both sides of the flanged portions of the cannulas, a diaphragm on both sides being preferred.

Referring still to the drawings, the illustrated apparatus is shown to contain, as a bottom member, a collection chamber 40 for receiving liquid drawn through the application plate 10, the membrane 16 and the holes 24 in the support plate 14. To receive liquid, the collection chamber is open on the upper side thereof which faces the bottom surface of the membrane support plate.

Figure 2:
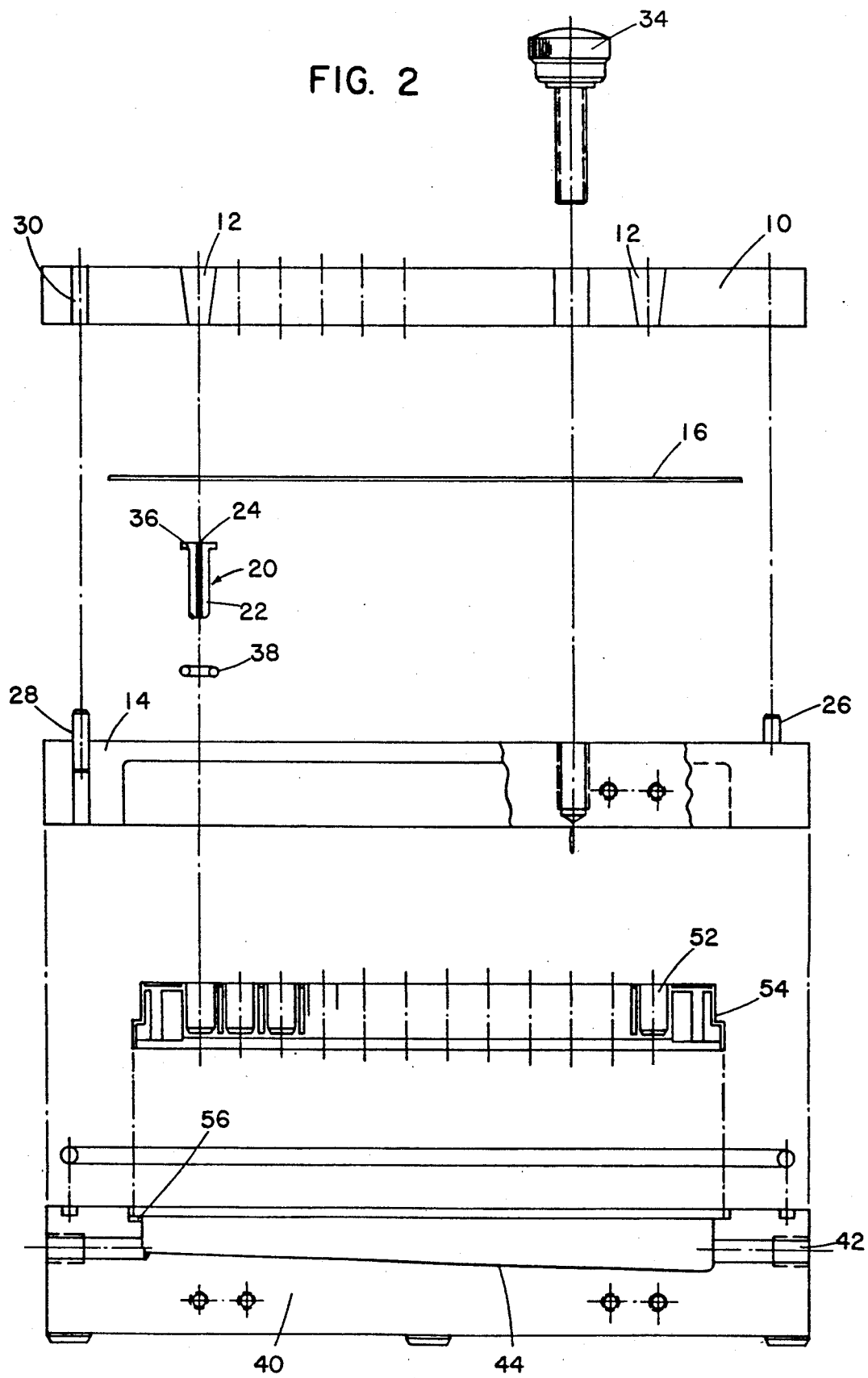
FIG. 2 is an exploded side elevation with certain parts broken away and shown in section.

To enable vacuum to be created within the chamber to draw liquid through the apparatus, the chamber contains the vacuum port 42 which is attached via tubing and valving to a vacuum pump such as a peristaltic pump. As illustrated in FIGS. 2 and 3, the bottom internal surface 44 of the collection chamber 40 is sloped to permit fluid to flow to the vacuum port and, in turn, be removed from the chamber 40. The chamber 40 also contains a port 46 which contains a valve (not shown) to relieve vacuum in the chamber after each sample solution (i.e., receptor, ligand, etc.) has been drawn through the membrane. By so doing, the succeeding solution placed in all of the holes of the application plate can be drawn simultaneously through the membrane by vacuum created by the peristaltic pump.

As indicated above, the final step in the assay procedure described herein involves collecting the colored liquid reaction product of substrate and enzyme so that color can be measured and, in turn, the amount of bound target ligand determined. To that end, there is provided for insertion into the chamber a microtiter plate 50 containing a plurality of wells 52 for collection of liquid. As illustrated, the lower portion of the microtiter plate contains a skirt 54 which, when the plate is inserted into the chamber 40, rests upon the ledge 56 in the chamber. In order to permit the vacuum created in the chamber 40 to communicate with the upper and middle portions of the apparatus and thereby permit drawing of the liquid through the apparatus, the ledge 56 is, as indicated, discontinuous between points 58 and 60 Thus, when a vacuum is drawn in the chamber 40, the microtiter plate does not form a vacuum tight seal with the ledge 56.

As shown in FIG. 3, when the microtiter plate 50 is contained within the collection chamber 40, the end of the sidewall extension of the cannulas 20 is located within the wells 52 of the microtiter plate 50. The extent to which the end of the cannulas so extend into the wells is such that when the assay procedure is completed and the colored reaction product of substrate and enzyme has been drawn into the wells 52, the end of the cannulas are submerged below the surface of the liquid. By so doing, when the membrane support plate and, in turn, the cannulas are withdrawn from the wells, the reservoir of liquid in the wells prevents drops from being retained on the ends of the cannulas, which drops may vary in volume from cannula to cannula. If drops were permitted to remain on the cannulas, the amount of solution transferred from the cannulas into the wells would be different, from well to well, and precise quantitation of bound ligand, from well to well, would not be obtainable.

Figure 4:
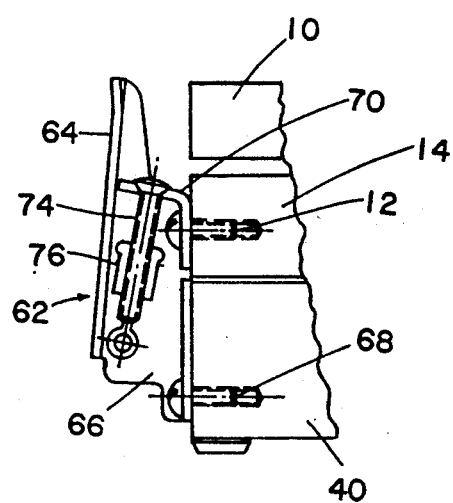
FIG. 4 is an enlargement, partly in section, of one of the clamps.
Figure 5:
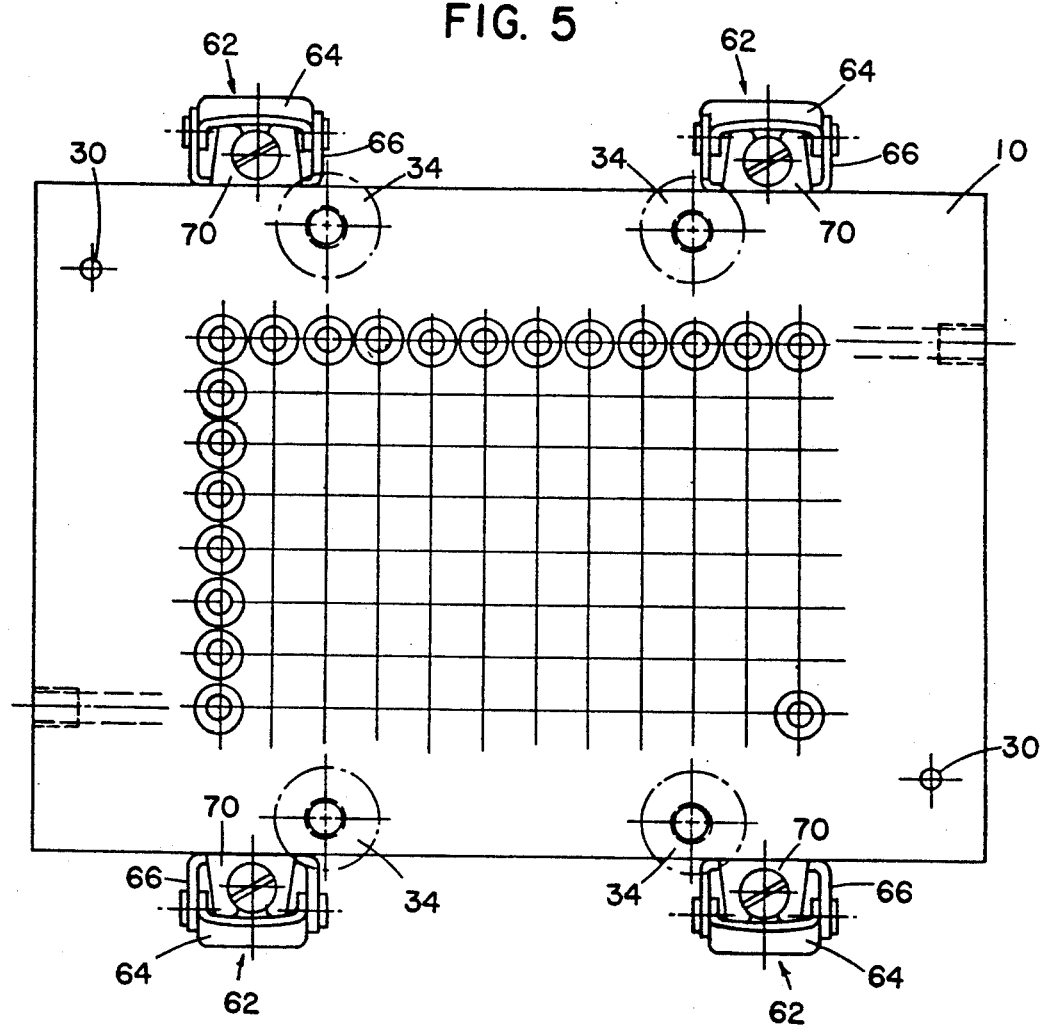
FIG. 5 is a top plan view of the assembled apparatus.
Figure 6:
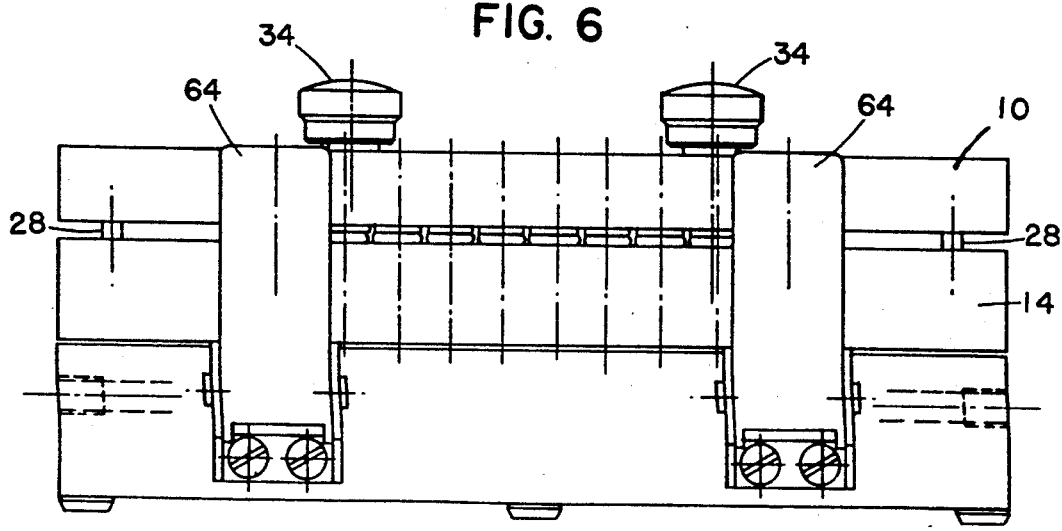
FIG. 6 is a side elevation, of view of the assembled apparatus.

The collection chamber is secured in vacuum tight relationship to the membrane support plate 14 by means of conventional clamping and gasketing. An example of such is shown in the drawings to include clamps 62 and gasket 48. Turning specifically to the clamps 62, they are shown in FIG. 4 to include a lever 64, a bracket 66 which is secured to the collection chamber 40 by means of the screws 68, a bracket 70 which is secured to the membrane support plate by means of the screws 72, and a tension screw 74 adjustably mounted in the housing 76. The housing 76 is pivotally mounted at the base of the lever 64 which, in turn, is pivotally mounted on the bracket 66. The upper bracket 70 is slotted to accommodate the head of the screw 74.

To clamp the chamber 40 to the support plate 14 using the clamps 62, the head of the screw 74 is inserted into the slot of the bracket 70 by pivoting the screw into position. Then, the lever 64 is raised, thus forcing the screw and, in turn, the bracket 70 downward to, in combination with the gasket 48, to effectively seal the chamber to the membrane support plate. By adjusting the screw within the housing 76, the tension can be adjusted to insure a vacuum seal.

The following example illustrates the use of the above described apparatus. All parts of the apparatus, except for the thumb screws and clamps, were made of plastic and a peristaltic pump was used to create vacuum. A commercially available nitrocellulose membrane sold for use in immunoassays was employed. Prior to insertion between the sample application plate and the support plate, the membrane was wetted with distilled water. The apparatus When assembled measured about $6\frac{1}{2}'' \times 4\frac{1}{2}''$ and was approximately $2\frac{1}{2}''$ high. 96 conically shaped holes were present in the application plate. The membrane support plates contained 96 cannulas as illustrated. A commercially available microtiter plate with 96 wells was used. The procedure employed was as follows.

100 $\mu$l of distilled water was placed into each of the 96 holes in the sample application plate. To expel air from the system, the distilled water was drawn by vacuum through the apparatus into the collection chamber and removed through the vacuum port. When the holes in the application plate are emptied of liquid and air first contacts the membrane, no further flow of liquid or air can occur because of capillarity. Thus, throughout the procedure, there remains a continuous liquid phase between the lower surface of the membrane and the bottom of the cannulas.

200 $\mu$l of human serum albumin (HSA) solution (50 $\mu$g/ml in Tris buffer) was then placed in each of the holes in the application plate. The peristaltic vacuum pump was started and over a period of five minutes the HSA solution was drawn through the apparatus and discharged into the collection chamber.

The vacuum relief valve was then opened and again closed after which time 200 $\mu$l of a 3% bovine serum albumin (BSA) solution was added to each of the holes in the application plate. Over a five minute period, the BSA solution was drawn through the membrane and discharged into the collection chamber, this step serving to block the vacant binding sites on the membrane. Again, the vacuum relief valve was opened and closed. Next, 200 $\mu$l of a 1:1000 dilution (in Tris buffer) of mouse derived anti-HSA was deposited into each of the holes in the application plate and drawn through the membrane and discharged into the chamber over a five minute period. After again opening and closing the vacuum relief valve, 200 $\mu$l of a 1:1000 dilution of goat derived anti-mouse IgG alkaline phosphatase conjugate solution was deposited into each of the holes in the application plate and over a five minute period drawn through the apparatus and discharged into the collection chamber. After again opening and closing the vacuum relief valve, unbound conjugate was removed from the membrane by washing the membrane three times with 200 $\mu$l of Tris buffer drawn through the membrane in thirty second intervals.

Subsequent to the foregoing washing step, the vacuum relief valve was opened and the collection chamber separated from the top assembly of the apparatus containing the application plate, membrane and membrane support plate. The chamber was emptied of any liquid remaining from the foregoing operations and the top assembly was placed on a piece of paper toweling to remove any excess liquid off the bottom of the cannulas. A commercially available 96 well flat bottomed microtiter plate was placed in the collection chamber and the apparatus reassembled by clamping the collection chamber and the membrane support plate together. As so assembled, the bottom of the cannulas extend into the wells of the microtiter plate. After closing the vacuum relief valve, 200 $\mu$l of a 0.5 mg/ml p-nitrophenyl phosphate solution was added to the wells and drawn through the apparatus over a five minute period. The colored solution produced by the reaction of substrate and enzyme was collected in the wells of the microtiter plate with the solution extending above the end of the cannulas positioned in the wells.

After the above procedure was completed, vacuum was relieved and the chamber was again separated from the membrane support plate. The cannulas were slowly withdrawn from the wells so that there was no remaining liquid on the exterior of the cannulas. The microtiter plate was then removed from the chamber and the color in each well read using a commercially available automatic ELISA plate reader. The amount of color determined in each well was substantially the same indicating the precision of the assay since equal quantities of mouse derived anti-HSA (the target ligand) were applied to each hole in the application plate.

While, in the foregoing procedure, a standard known concentration of target ligand was employed, an unknown amount of target ligand can be identified by using the above protocol. In this instance, instead of one standard known concentration of target ligand being employed, an entire range of known concentrations or target ligands are utilized, thereby yielding plotted data which correlates color development with the known concentrations of target ligands in a standard curve. The standard curve is then used to translate the color development of an unknown concentration of target ligand to its actual concentration. In practice, unknown samples can fill a number of the holes in the application plate and the balance of the holes can contain the standard solutions for construction of the standard curve.

Although the protocol illustrated as an example above is commonly called a direct sandwich assay, the apparatus and methodology herein described is not limited to this type of assay. It can also be used in direct assays, indirect assays, indirect sandwich assays, competitive assays, etc. Essentially any immunoassay arrangement used with standard ELISA type techniques can be mimicked with the apparatus and methodology described herein.

What is claimed is:

1. An apparatus for use in a ligand-receptor assay procedure for the quantitative determination of the concentration of a target ligand in a liquid sample, said apparatus comprising a top member, a middle member, and a bottom member in a sandwiched relationship, said top and middle members being plates having a plurality of holes therethrough with said holes in the two plates being in axial alignment and with the cross-sectional area of the holes at the bottom surface of the top plate being greater than the cross-section area of the holes at the top surface of the middle plate, the holes in said middle plate receiving cannulas extending below the bottom surface of the middle plate, said bottom member being a chamber having an opening on the upper side thereof facing the bottom surface of said middle plate, said chamber containing (1) at least one port extending through a surface thereof to permit a vacuum to be created within said chamber and (2) a microtiter plate containing a plurality of wells positioned within the chamber such that the ends of the cannulas extending beneath the bottom surface of the middle plate are located within said wells with the degree of extension within said wells of the microtiter plate being such that the ends of the cannulas are in close proximity and just above the bottom of the wells so that liquid deposited in said wells extends above the ends of the cannulas, said apparatus containing means for securing said three members together in vacuum tight relationship with a liquid permeable member placed between the top and middle plates, such that when a liquid is placed in the holes in the top plate and vacuum is created in the chamber, the liquid is drawn at a controlled rate directly through the membrane without lateral dispersion, through the cannulas in the middle plate and, in turn, into the chamber.

2. The apparatus of claim 1 wherein said membrane being capable of binding the receptor utilized in the assay procedure.

3. The apparatus of claim 1 wherein the microtiter plate is positioned within the chamber.

4. The apparatus of claim 1 wherein the sidewalls of the cannulas extend above the top surface of the middle plate, the top end of the cannulas containing a flanged portion.

5. The apparatus of claim 4 wherein said membrane being capable of binding the receptor utilized int he assay procedure.

6. The apparatus of claim 5 wherein the microtiter plate is positioned within the chamber.

7. The apparatus of claim 6 wherein the membrane is nitrocellulose.

* * * * *